United States Patent [19]

Regan et al.

[11] Patent Number: 4,904,692
[45] Date of Patent: Feb. 27, 1990

[54] NOVEL HMG-COA REDUCTASE INHIBITORS

[75] Inventors: John R. Regan, Princeton, N.J.; Josehp G. Bruno, Sellersville, Pa.; Kent W. Neuenschwander, Ambler, Pa.; Donald E. Kuhla, Doylestown, Pa.

[73] Assignee: Rorer Pharmaceutical Corporation, Fort Washington, Pa.

[21] Appl. No.: 283,111

[22] Filed: Dec. 12, 1988

Related U.S. Application Data

[63] Continuation-in-part of Ser. No. 135,805, Dec. 21, 1987, Pat. No. 4,863,957.

[51] Int. Cl.$^4$ .................. A61K 31/365; C07D 309/30
[52] U.S. Cl. .................................... 514/459; 514/460; 514/824; 549/292
[58] Field of Search ................ 549/292; 514/459, 460, 514/824

[56] References Cited

U.S. PATENT DOCUMENTS

| | | | |
|---|---|---|---|
| 4,282,155 | 8/1981 | Smith et al. | 549/292 |
| 4,375,475 | 3/1983 | Willard et al. | 549/292 |
| 4,567,289 | 1/1986 | Willard et al. | 560/59 |
| 4,611,067 | 9/1986 | Volante et al. | 556/416 |
| 4,622,338 | 11/1986 | Baron et al. | 514/460 |
| 4,668,699 | 5/1987 | Hoffman et al. | 549/292 |
| 4,681,893 | 7/1987 | Roth | 514/423 |

Primary Examiner—Richard L. Raymond
Assistant Examiner—Mark W. Russell
Attorney, Agent, or Firm—Imre (Jim) Balogh; James A. Nicholson

[57] ABSTRACT

Disclosed are novel 3-hydroxy-3-methylglutaryl-coenzyme A reductase inhibitors useful as antihypercholesterolemic agents represented by the formula

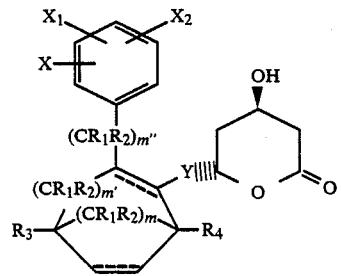

and the corresponding ring-opened hydroxy acids derived therefrom and pharmaceutically acceptable salts thereof.

Pharmaceutical compositions containing said compounds and method of inhibiting the biosynthesis of cholesterol therewith are also disclosed.

25 Claims, No Drawings

NOVEL HMG-COA REDUCTASE INHIBITORS

This application is a continuation-in-part application of United States Pat. Application Ser. No. 135,805, filed Dec. 21, 1987 now U.S. Pat. No. 4,863,957.

BACKGROUND OF THE INVENTION

1. Field of the Invention

The present invention relates to compounds, pharmaceutical compositions and a method useful for reducing serum cholesterol in humans. More particularly, the invention relates to trans-6-[2-[aryl and arylalkylbicyclo[a.2.b]-alk(en)yl]-alk(en)yl]-3,4,5,6-tetrahydro-4-hydroxy-2H-pyran-2-ones, the corresponding ring opened hydroxy acids derived therefrom and pharmaceutically acceptable salts thereof which are potent inhibitors of the enzyme 3-hydroxy-3-methylglutaryl-coenzyme A reductase (hereinafter HMG-CoA reductase), pharmaceutical compositions thereof, and a method of inhibiting biosynthesis of cholesterol for the treatment of atherosclerosis, hyperlipidemia and hypercholesterolemia.

2. Related Prior Art

Inhibitors of HMG-CoA are effective in lowering blood plasma cholesterol level as well as inhibiting the biosynthesis of cholesterol in humans. As such, inhibitors of HMG-CoA are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6-[2-(3-or 4-carboxamido-substituted pyrrol-1-yl)alkyl]-4-hydroxypyran-2-ones useful as hypochloesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,282,155 to Smith et al. is directed to 6(R)-[2-(8'-Etherified-hydroxy-2',6'-dimethylpolyhydronaphtyl-1') ethyl]-4(R)-hydroxy-3,4,5,6-tetrahydro-2H-pyran-2-ones for inhibition of biosynthesis of cholesterol.

U.S. Pat. No. 4,567,289 relates to methyl, ethyl, n-propyl, 2-(acetylamino)ethyl, or 1-(2,3-dihydroxy)propyl ester of E-(3R,5S)-7-(4,-fluoro-3,3',5-trimethyl[1,1'-biphenyl]-2-yl)-3,5-dihydroxy-6-heptenoic acid that are HMG-CoA reductase inhibitors.

U.S. Pat. No. 4,611,067 discloses a process for the preparation of HMG-CoA reductase inhibitors which contain a 4-hydroxy-3,4,5,6-tetrahydro-2H-pyran-2-one moiety.

SUMMARY OF THE INVENTION

In accordance with the present invention, certain trans-6-[2-[aryl and arylalkylbicyclo[a.2.b]alk(en)yl]alk(en)yl]-3,4,5,6-tetrahydro-4-hydroxy-2H-pyran-2-ones, the corresponding ring-opened hydroxy-acids derived therefrom and pharmaceutically acceptable salts thereof are provided which are potent inhibitors of HMG-CoA reductase. Specifically, the invention provides compounds of the formula

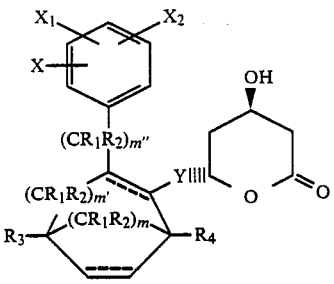

and pharmaceutically acceptable salts thereof; wherein
Y is: —CHR—,
—HRCHR—,
—CHRCHRCHR—, or
—RC=CR—;
X, $X_1$ and $X_2$ are independently: H, F, Cl, Br, OH, $CF_3$ alkyl, alkoxy, aryl, $NO_2$, NH(CO)R, $N(R)_2$, or $S(O)_nR$;
R, $R_1$, $R_2$, $R_3$ and $R_4$ are independently: H or lower alkyl;
m is: 1 or 2;
m' is: 0 or 1;
m" is: 0 or 1;
n =0, 1, 2; and
the dotted lines in the bicyclic ring represent optional double bonds.

DETAILED DESCRIPTION OF THE INVENTION

As employed above and throughout the specification, the following terms, unless otherwise indicated, shall be understood to have the following meaning:

"Lower alkyl" means a saturated or unsaturated aliphatic hydrocarbon which may be either straight—or branched-chained containing from 1 to 4 carbon atoms.

"Alkyl" means a saturated or unsaturated aliphatic hydrocarbon which may be either straight-or branched-chained containing from about one to about six carbon atoms.

"Alkoxy" means an alkyl oxy group in which "alkyl" is as previously defined. Lower alkoxy groups are preferred which include methoxy, ethoxy, n-propoxy, i-propoxy, sec-propoxy, and n-butoxy.

"Aryl" means an aromatic hydrocarbon radical having 6 to 10 carbon atoms. The preferred aryl groups are phenyl, substituted phenyl and naphthyl. The term "substituted" means "alkyl" substitution.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and stereoisomers of the compounds and mixtures thereof defined by the structural formula.

The general procedure for producing the compounds of the present invention is as follows:

Reaction Sequence

Reaction sequences A and B, corresponding with Examples 1 and 2 respectively, illustrate the general methods for synthesizing the compounds of the present invention.

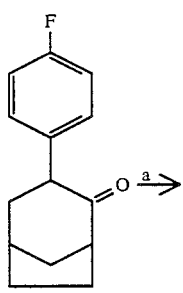
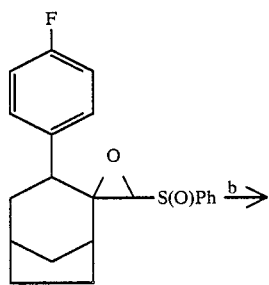
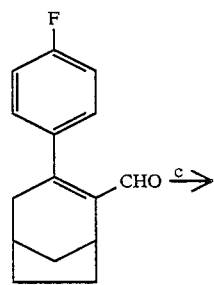
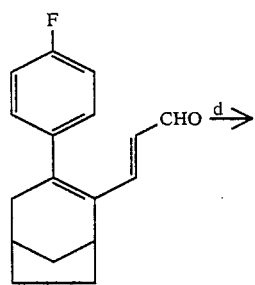
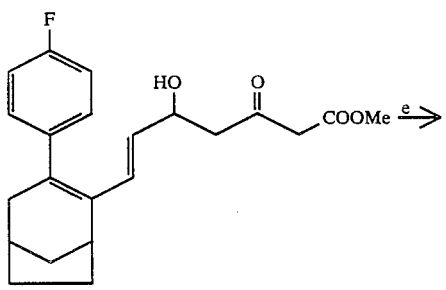
A. 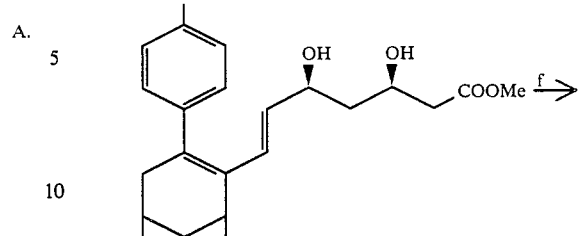
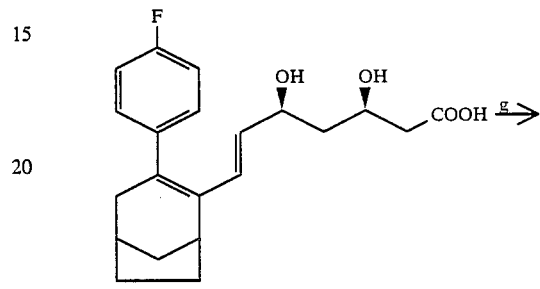
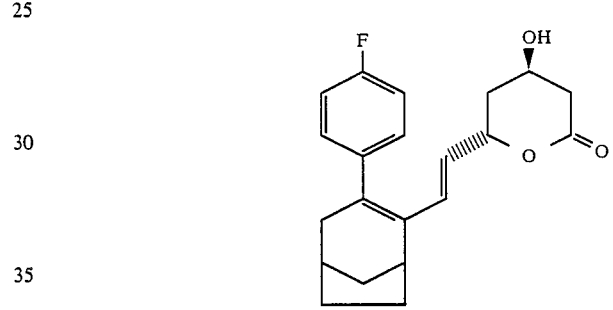
LEGEND:
a: (1) PhS(O)CH$_2$Cl/n-butyl lithium/THF, (2) KOH/methanol
b: BF$_3$-etherate/CH$_2$Cl$_2$
c: C$_6$H$_{11}$N=CHCH$_3$/LDA/THF/SiO$_2$
d: Methyl acetoacetate/NaH/n-butyl lithium/THF
e: (1) BEt$_3$/THF, (2) NaBH$_4$, (3) methanol, (4) H$_2$O$_2$/H$_2$O
f: NaOH/H$_2$O/methanol
g: 1,3-Dicyclohexylcarbodiimide/ether
B.
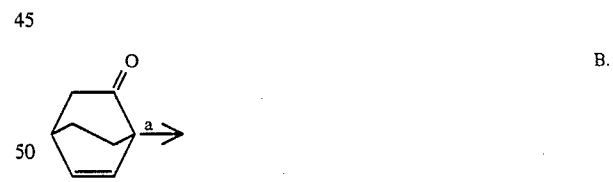
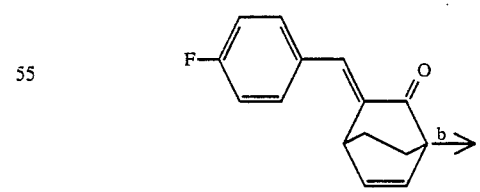
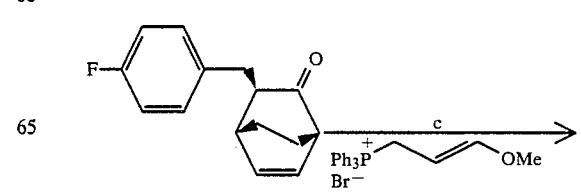

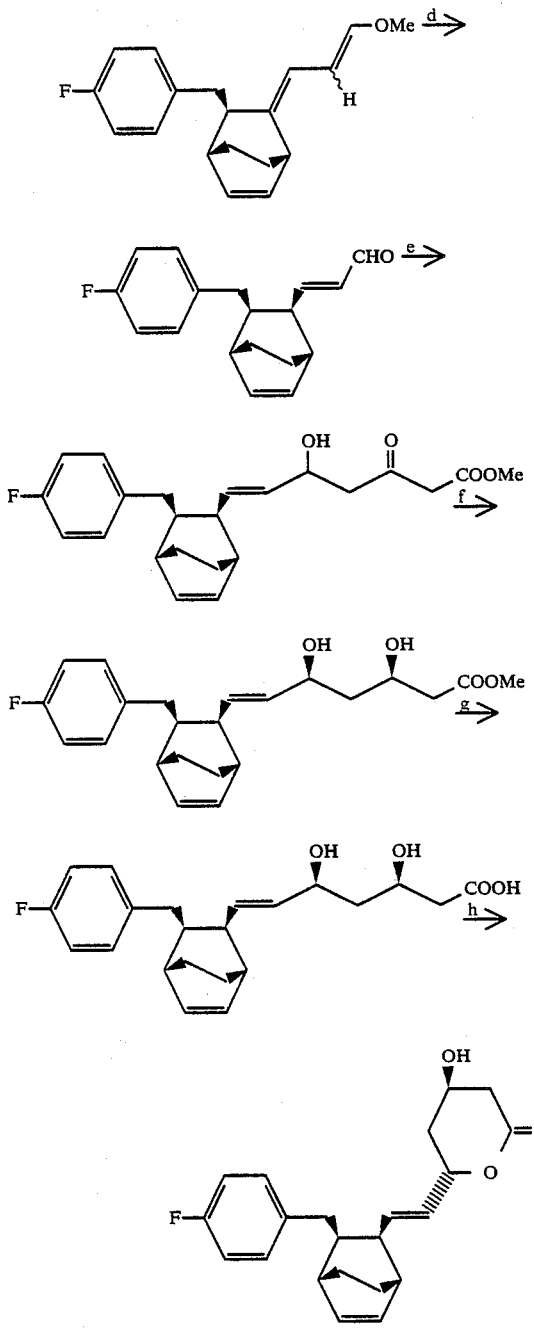

LEGEND
a: 4-F—C$_6$H$_4$—CHO/KOH/2-propanol/heat
b: Zn/CH$_3$COOH/THF
c: n-butyl lithium/THF
d: HCl/H$_2$O/THF
e: Methyl acetoacetate/NaH/n-butyl lithium/THF
f: (1) BEt$_3$/THF, (2) NaBH$_4$, (3) methanol, (4) H$_2$O$_2$/H$_2$O
g: NaOH/H$_2$O/methanol
h: CHCl$_3$/reflux The starting materials were obtained from the Aldrich Chemical Co. or they may also be synthesized in accordance with methods known in the art.

The following preparative examples will further illustrate the invention.

EXAMPLE 1

Step 1: Preparation of 3-(4-fluorophenyl)bicyclo3.2.11-octane-2-spiro-(2,-oxirane)

To a solution of chloromethyl phenyl sulfoxide (3.70 g, 21.2 mmoles) in anhydrous tetrahydrofuran (THF) at −78° C. and under a N$_2$ atmosphere was added n-butyl lithium (8.5 ml of a 2.5M solution in hexane, 21.2 mmoles) dropwise. The solution was stirred for 10 minutes and a solution of 2-(4-fluorophenyl)-1-oxobicyclo[3.2.1]octane (Tetrahedron Letters, 52 5327 (1967)) (4.40 g, 20.2 mmoles) in 20 ml THF was added. The solution was stirred for 60 minutes and diluted with ether and water. The organic layer was washed with water, dilute aqueous HCl, saturated NaHCO$_3$ and brine and dried (MgSO$_4$). Removal of the volatiles in vacuo provided a residue which was treated with 100 ml of 20% KOH in methanol for 10 minutes. The volatiles were removed in vacuo and the residue was diluted with ether and water. The organic layer was washed with water and brine and dried (MgSO$_4$). Removal of the volatiles in vacuo provided a residue which was recrystallized with hexes in ethyl acetate and provided 5.38 g of product. mp 178°–180° C.

Step 2: Preparation of 3-(4-fluorophenyl)bicyclo3.2.11oct-2-ene-2-carboxaldehyde A solution of 3-(4-fluorophenyl)bicyclo[3.2.1]octane-2-spiro-(2'-oxirane) (5.1 g) and 5.1 ml of BF$_3$ etherate in 50 ml CH$_2$Cl$_2$ was stirred at 25° C. for 18 hours and diluted with ether and water. The organic layer was washed with brine and dried (MgSO$_4$). Removal of the volatiles in vacuo provided a residue which was purified by HPLC using 40/1 hexanes/ethyl acetate as the eluent. Concentration in vacuo of the product rich fractions provided the product as an orange oil.

Step 3: Preparation of 3-[3-(4-fluorophenyl)bicyclo[3.2.1]oct-2-en-2-yl]-propenal To a 0°–5° C. solution of LDA (26.5 mmoles) in 25 ml anhydrous ether was added ethylidenecyclohexylamine (Org. Syn. 50 66) (3.32 g, 26.5 mmlles) in 25 ml anhydrous ether. The solution was stirred for 10 minutes, cooled to −70° C. and 3-(4-fluorophenyl)bicyclo[3.2.-1]oct-2-ene-2-carboxaldehyde (5.55 g, 24.1 mmoles) in 25 ml ether was added. The solution was stirred for 60 minutes, warmed to 0°–5° C., stirred for 90 minutes and diluted with water. The organic layer was washed with water and brine and dried (MgSO$_4$). Removal of the volatiles in vacuo provided a residue which was purified by HPLC using 3% ethyl acetate in hexanes as the eluent. Concentration in vacuo of the product rich fractions provided 2.53 g of the product as an orange oil.

Step 4: Preparation of methyl (E)-7-[3-[4-fluorophenyl)bicyclo3.2.1]oct-2-en-2-yl]-5-hydroxy-3-oxohept-6-enoate To a 0°–5° C. suspension of pentane-washed sodium hydride (0.43 g, 10.6 mmoles) in 10 ml anhydrous THF was added dropwise methyl acetoacetate. The solution was stirred for 30 minutes and n-butyl lithium (5.8 ml of a 1.6M solution in hexanes, 9.31 mmoles) was added dropwise. The solution was stirred for 20 minutes and a solution of 3-[3-(4-fluorophenyl)bicyclo[3.2.1]oct-2-en- 2-yl]propenal (2.50 g, 9.75 mmoles) in 15 ml anhydrous THF was added. The resulting solution was stirred for 60 minutes and quenched with ether and aqueous HCl. The organic layer was washed with water and brine and dried (MgSO$_4$). Removal of the volatiles in vacuo provided 3.3 g of the solid product which was used without further purification.

Step 5: Preparation of methyl (E)-7-[3-(4-fluorophenyl)bicyclo[3.2.1]oct-2-en-2-yl]-3,5-dihydroxyhept-6-enoate To a solution of methyl (E)-7-[3-(4-fluorophenyl)-bicyclo[3.2.1]oct-2-en-2-yl]-5-hydroxy-3-oxohept-6-enoate (2.85 g, 7.65 mmoles) in 12 ml anhydrous THF was added triethylborane (11.5 ml of a 1M THF solution, 11.5 mmoles). The mixture was stirred for 5 minutes and cooled to $-78°$ C. Sodium borohydride (0.333 g, 8.8 mmoles) was added followed by the dropwise addition of 5 ml methanol. The mixture was stirred for 60 minutes and quenched with the dropwise addition of aqueous H$_2$O$_2$ (12 ml of 30% H$_2$O$_2$ in 27 ml H$_2$O). The mixture was warmed to 25° C. during 90 minutes and poured into a mixture of ethyl acetate and aqueous HCl. The organic layer was washed with water and brine and dried (MgSO$_4$). Removal of the volatiles in vacuo provided a residue which was purified by HPLC using 60% hexanes in ethyl acetate. The product rich fractions were concentrated in vacuo and provided 1.32 g of the oily product.

Step 6: Preparation of (E)-7-[3-(4-fluorophenyl)bicyclo-3.2.1]oct-2-en-2-yl]-3,5-dihydroxyhept-6-enoic acid A solution of methyl (E)-7-[3-(4-fluorophenyl)bicyclo[3.2.1]oct-2-en-2-yl]-3,5-dihydroxy-hept-6-enoate (1.30 g, 3.47 mmoles) and aqueous NaOH (5.2 ml of a 1N solution) in 15 ml methanol was stirred for 30 minutes at 25° C., cooled to 0°-5° C., acidified, diluted with water and extracted with ethyl acetate. The organic layers were washed with brine and dried (MgSO$_4$). Removal of the volatiles in vacuo provided 1.28 g of the solid product which was used without further purification.

Step 7: Preparation of trans-(E)-6-[2-[3-(4-fluorophenyl)bicyclo[3.2.1]oct-2-en-2-yl]-ethenyl]-3,4,5,6-tetrahydro-4-hydroxy-2H-oyran-2-one To a solution of 7-[3-(4-fluorophenyl)bicyclo[3.2.1]-oct-2-en-2-yl]-3,5-dihydroxyhept-6-enoio acid (1.28 g, 3.55 mmoles) in 15 ml anhydrous ether at 0°-5° C. was added dicyclohexylcarbodiimide (0.74 g, 3.55 mmoles). The mixture was stirred for 4 hours, filtered and the volatiles were removed in vacuo. Purification of the residue using silica gel and 60% hexanes in ethyl acetate as the eluent provided 0.518 g of the solid product. mp 123°-127° C.

EXAMPLE 2

Step 1: Preparation of 3-(4-fluorobenzylidene)bicyclo[2.2.2]oct-5-en-2-one

A solution of bicyclo[2.2.2]oct-5-en-2-one (J. Oro. Chem. 33, 2211 (1968)) (3.34 g, 27.4 mmoles), 4-fluorobenzaldehyde (3.08 ml, 28.7 mmoles) and KOH (2 pellets) in 10 ml of 2-propanol was heated at 60° C. for 1.5 hours, cooled to room temperature and diluted with H$_2$O and ether. The organic layer was washed with H$_2$O, 2% aqueous HCl, saturated NaHCO$_3$ and brine and dried (MgSO$_4$). Removal of the volatiles in vacuo provided a residue which was recrystallized with hexanes. mp 85°-86° C.

Step 2: Preparation of exo-3-(4-fluorophenylmethyl)bicyclo[2.2.2p90 oct-5-en-2-one A mixture of 3-(4-fluorobenzylidine)bicyclo[2.2.2]oct-5-en-2-one (1.68 g, 7.37 mmoles), zinc dust (4.79 g, 73.7 mmoles) and glacial acetic acid (4.2 ml, 73.7 mmoles) in 35 ml anhydrous tetrahydrofuran (THF) was stirred at ambient temperature for 4 hours and filtered through celite. The filtrate was concentrated in vacuo. The residue was diluted with ethyl acetate, washed with H$_2$O, saturated NaHCO$_3$ and brine and dried (MgSO$_4$). Removal of the volatiles in vacuo provided a residue which was purified by silica gel chromatography using 10% ethyl acetate in hexanes as the eluent. Concentration in vacuo of the product rich fractions provided the product (1.33g) as an oil.

Step 3: Preparation of exo-3-(4-fluorophenylmethyl)-2-(3-methoxy-2-propenylidene)bicyclo2.2.2]oct-5-ene To a solution of 3-methoxy-2-propenyltriphenylphosphonium bromide (5.59 g, 13.6 mmoles) in 50 ml anhydrous THF at $-40°$ C. was added dropwise n-butyl lithium (5.43 ml of a 2.5M solution in hexanes, 13.6 mmoles). The solution was stirred 1.5 hours and exo-3-(4-fluorophenylmethyl)bicyclo[2.2.2]oct-5-en-2-one (2.08 g, 9.04 mmoles) in 20 ml anhydrous THF was added dropwise. The mixture was slowly warmed to ambient temperature, stirred overnight, and diluted with ether and aqueous HCl. The organic layer was washed with H$_2$O, saturated NaHCO$_3$ and brine and dried (MgSO$_4$). Removal of the volatiles in vacuo provided a residue which was purified by HPLC using 2% ethyl acetate in hexanes as the eluent. Concentration in vacuo of the product rich fractions provided 1.14 g of the oily product as a mixture of (E)- and (Z)-isomers.

Step 4: Preoration of (E)-3-[cis-exo-3-(4-fluorophenylmethyl)bicyclo[2.2.2]oct-5-en-2-yl]propenal A solution of exo-3-(4-fluorophenylmethyl)-2-(3-methoxy-2-propenylidene)bicyclo[2.2.2]oct-5-ene (1.4 g) in 25 ml THF and 3 ml of 4N HCl was stirred for 5 days and the volatiles were removed in vacuo. The residue was diluted with ether, washed with H$_2$O, saturated NaHCO$_3$ and brine and dried (MgSO$_4$). Removal of the volatiles in vacuo provided a residue which was purified by silica gel chromatography using 5% ethyl acetate in hexanes as the eluent. Concentration in vacuo of the product rich fractions provided 0.60 g of the oily product.

Step 5: Preparation of methyl (E)-7-[cis-exo-3-(4-fluorophenylmethyl)bicyclo[2.2.2]oct-5-en-2-yl]-5-hydroxy-3-oxo-hept-6-enoate To a slurry of pentane-washed NaH (94 mg of 60%, 2.34 mmoles) in 1.5 ml anhydrous THF at 0°-5° C. was added dropwise methyl acetoacetate (0.21 ml, 1.95 mmoles). The solution was stirred for 30 minutes and n-butyl lithium (0.82 ml of a 2.5M solution in hexanes, 2.0 mmoles) was added dropwise. The solution was stirred for 15 minutes and a solution of (E)-3-[cis-exo-3-(4-fluorophenylmethyl)bicyclo[2.2.2]oct-5-en-2- yl]propenal (0.58 g, 2.15 mmoles) in 5 ml anhydrous THF was added. The solution was stirred for 90 minutes and quenched with 4N HCl and ether. The organic layer was washed with H₂O, saturated NaHCO₃ and brine and dried (MgSO₄). Removal of the volatiles in vacuo provided a residue which was purified by silica gel chromatography using 25% ethyl acetate in hexanes. Concentration in vacuo of the product rich fractions provided 0.23 g of the oily product.

Step 6: Preparation of methyl (E)-7-[cis-exo-3-(4-fluorophenylmethyl)bicyclo[2.2.2]oct-5-en-2-yl]-3,5-dihydroxy-hept-6-enoate A solution of methyl (E)-7-[cis-exo-3-(4-fluorophenylmethyl)bicyclo[2.2.2]oct-5-en-2-yl]-5-hydroxy-3-oxohept-6-enoate (0.22 g, 0.57 mmoles) and triethylborane (0.85 ml of 1M THF solution, 0.85 mmoles) was stirred for 10 minutes and cooled to −78° C. and NaBH₄ (32 mg, 0.85 mmoles) was added, followed by the dropwise addition of methanol (0.4 ml) over 5 minutes. The solution was stirred for 30 minutes, quenched with H₂O₂ (1.0 ml of 30% in 2.5 ml H₂O), warmed to ambient temperature and stirred for 30 minutes. The solution was diluted with ethyl acetate and aqueous HCl. The organic layer was washed with H₂O and brine and dried (MgSO₄). Removal of the volatiles in vacuo provided a residue which was purified by silica gel chromatography using 50% ethyl acetate in hexanes as the eluent. Concentration in vacuo of the product rich fractions provided 0.18 g of the oily product.

Step 7: Preparation of trans-(E)-6-2-[cis-exo-3-(4-fluorophenylmethyl)bicyclo2.2.2]oct-5-en-2-yl]ethenyl1-3,4,5,6-tetrahydro-4-hydroxy-2H-oyran-2-one To a solution of methyl (E)-7-[cis-exo-3-(4-fluorophenylmethyl)bicyclo[2.2.2]oct-5-en-2-yl]-3,5-dihydroxyhept-6-enoate (0.15 g) in 3 ml methanol at 0°–5° C. was added 0.2 ml of 2N NaOH. The solution was stirred for 6 hours and the volatiles were removed in vacuo. The residue was diluted with water, acidified to pH 2 and extracted with ethyl acetate. The organic extracts were combined, washed with brine and dried (MgSO₄). Removal of the volatiles in vacuo provided a residue which was diluted with 4 ml CHCl₃. The solution was heated at reflux for 16 hours and the volatiles were removed in vacuo. Purification of the residue by silica gel chromatography using 33% ethyl acetate in hexanes as the eluent provided the product. mp 144°–146° C.

Employing the general methods detailed in Examples 1 and 2 the following compounds can be made:

trans-(E)-6-[2-[3-(4-fluoro-3-methylphenyl)-1,5,8,8-tetramethylbicyclo[3.2.1]oct-2-en-2-yl]ethenyl]-3,4,5,6-tetrahydro-4-hydroxy-2H-pyran-2-one;

trans-(E)-6-[2-[3-(4-fluoro-3-chlorophenyl)-1,5-di-(1methylethyl)bicyclo[3.2.1]oct-2-en-2-yl]ethenyl]-3,4,5,6-tetrahydro-4-hydroxy-2H-pyran-2-one;

trans-6-[2-[cis-endo-3-(4-methylphenyl)bicyclo[3.2.1]octan-2-yl]ethyl]-3,4,5,6-tetrahydro-4-hydroxy-2H-pyran-2-one;

trans-(E)-6-[2-[3-(4-fluoro-3-methylphenyl)-1,5-dimethylbicyclo[3.2.1]octa-2,6-dien-2-yl]ethenyl]-3,4,5,6-tetrahydro-4-hydroxy-2H-pyran-2-one;

(E)-7-[3-(4-trifluoromethylphenyl)-1,5-dimethylbicyclo[3.2.2]non-2-en-2-yl]-3,5-dihydroxyhept-6-enoic acid sodium salt;

(E)-7-[3-(4-fluorophenylmethyl)bicyclo[3.2.2]non-2-en-2-yl]3,5-dihydroxyhept-6-enoic acid sodium salt;

trans-(E)-6-[2-[cis-exo-3-(4-fluoro-3-methylphenyl)bicyclo[2.2.2]oct-5-en-2-yl]ethenyl]-3,4,5,6-tetrahydro-4-hydroxy-2H-pyran-2-one;

trans-(E)-6-[2-[3-(4-fluoro-3-methylphenyl)-1,4-dimethylbicyclo[2.2.2]octa-2,5-dien-2-yl]ethenyl]-3,4,5,6-tetrahydro-4-hydroxy-2H-pyran-2-one;

trans-(E)-6-[2-[trans-3-(3,4-ditrifluorophenyl)-1,4-di-(1methylethyl)bicyclo[2.2.2]octan-2-yl]ethenyl]-3,4,5,6-tetrahydro-4-hydroxy-2H-pyran-2-one;

trans-(E)-6-[3-(3-methylphenylmethyl)-1-methylbicyclo[2.2.2]oct-2-en-2-yl]ethenyl]-3,4,5,6-tetrahydro-4-hydroxy-2H-pyran-2-one;

(E)-7-[3-(4-fluorophenyl)-1,4-dimethylbicyclo[2.2.1]hepta2,5-dien-2-yl]-3,5-dihydroxyhept-6-enoic acid; and 7-[cis-exo-3-(4-chlorophenylmethyl)-1,4-dimethylbicyclo[2.2.1]heptan-2-yl]-3,5-dihydroxyheptanoic acid.

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course be given in two to four divided doses. With other forms of administration equivalent or adjusted doses will be administered depending on the route of administration.

The utility of the claimed compounds is measured by the test method described hereunder. The method is based on the articles: "Purification of 3-hydroxy-3-methylglutarylcoenzyme A reductase from rat liver" by Kleinsek et al., Proc. Natl. Acad. Sci. USA, Vol. No. 4, pp. 1431–1435, April 1977 Biochemistry; "Mevinolin: A highly potent competitive inhibitor of hydroxy methyl glutaryl-coenzyme A reductase and a cholesterol-lowering agent" by Alberts et al., Proc. Natl. Acad. Sci. USA, Vol 77, pp. 3951–3961, July 1980, Biochemistry; "Effects of ML-236B on cholesterol metabolism in mice rats: Lack of hypocholesterolemic activity in normal animals" by Endo et al., Biochimica et Biophysica Acta, 575 (1979) 266–276; and "Evidence of regulation of 3-hydroxy-3-methylglutaryl coenzyme A reductase activity and cholesterol synthesis in nonhepatic tissues of rat" by Balasubramaniam et al., Proc. Natl. Acad. Sci. USA, Vol. 73, No. 8, pp. 2564–2568, Aug. 1976, Biochemistry.

The method used (designated HMGR Screen) was as follows. Male rats were acclimated to an alternate 12 hour light-dark cycle for a period of 2–3 weeks. The animals, weighing 180–230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at −80° C. in 300 μl portion samples. Prior to use, the enzyme was activated at 37° C. for 30 minutes in a reaction mixture. The reaction mixture contained in a volume of 240 μl: 0.14 M potassium phosphate buffer (pH 7.0); 0.18 M KCl; 3.5 mM EDTA; 10 mM dithiothreitol; 0.1 mg/ml BSA; 30,000 cpm of [$^{14}$C]HMG-CoA; 20 μM HMG-CoA, and 200 μg of solubilized enzyme with and without inhibitors (in 10 μl DMSO). After 5 minutes incubation at 37° C. the reaction was initiated with 0.2 mM NADPH. The final assay volume was 300 μl. The reaction then was terminated with 100 μl of IN HCl. After an additional incubation for 15 minutes at 37° C. to allow for complete lactonization of the product, the mixture was diluted with 3 ml GDW. The diluted mixture was then poured over a 0.7×1.4 cm column containing 100–200 mesh Bio-Rex ion-exchange resin (chloride form of Bio-Rad) which was equilibrated with distilled water. With this resin the unreacted [$^{14}$C] HMG-CoA was adsorbed and the product [$^{14}$C]lactone was eluted (80% recovery) directly into scintillation vials. After the addition of 10 ml of Aquasol®, radioactivities of the samples were measured in a scintillation counter. The compounds tested were found to inhibit the enzyme of HMG-CoA reductase in the range of IC$_{50}$=0.5–10 μM and, therefore, can be used for the treatment and prevention of hypercholesterolemia, hyperlipoproteinemia and arteriosclerosis.

What is claimed is:

1. A compound of the formula

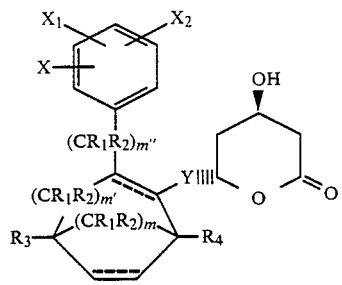

and the pharmaceutically acceptable salts thereof wherein

Y is: —CHR—,
—CHRCHR—,
—CHRCHRCHR—, or
—RC=CR—;

X, $X_1$ and $X_2$ are independently: H, F, Cl, Br, OH, CF$_3$ alkyl, alkoxy, aryl, NO$_2$, NH(CO)R, N(R)$_2$, or S(O)$_n$R;

R, $R_1$, $R_2$, $R_3$ and $R_4$ are independently: H or lower alkyl;

m is: 1 or 2;
m' is: 0 or 1;
m" is: 0 or 1;
n=0, 1, 2; and the dotted lines in the bicyclic ring represent optional double bonds.

2. A compound of claim 1 wherein X is fluoro and $X_1$ is lower alkyl.

3. A compound of claim 1 wherein X, $R_1$ and $R_2$ are alkyl of one to six carbon atoms.

4. A compound of claim 1 wherein X and $X_1$ are aryl and $X_2$ is trifluoromethyl.

5. A compound of claim 1 wherein at least one of the X, $X_1$ and $X_2$ radicals is phenyl.

6. A compound of claim 1 wherein at least one of the X, $X_1$ and $X_2$ radicals is substituted phenyl.

7. A compound of claim 1 wherein at least one of the X, $X_1$ and $X_2$ radicals is naphthyl.

8. A compound of claim 1 wherein R is lower alkyl having 1–4 carbon atoms.

9. A compound of claim 1 wherein $R_3$ and $R_4$ are lower alkyl.

10. A compound of claim 1 wherein m is 2, m' is 0 and m" is 1.

11. A compound of claim 1 wherein m is 1, m' is 1 and m" is 0.

12. A compound of claim 1 wherein Y is —CH=CH—.

13. A compound of claim 1 wherein Y is —CH$_2$CH$_2$—.

14. Trans-(E)-6-[2-[3-(4-fluorophenyl)bicyclo[3.2.1]oct-2-en-2-yl]ethenyl]-3,4,5,6-tetrahydro-4-hydroxy-2H-pyran-2-one.

15. Trans-(E)-6-[2-[cis-exo-3-(4-fluorophenylmethyl)bicyclo[2.2.2]oct-5-en-2-yl]ethenyl]-3,4,5,6-tetrahydro-4-hydroxy-2H-pyran-2-one.

16. Trans-(E)-6-[2-[3-(4-fluoro-3-methylphenyl)-1,5-dimethylbicyclo[3.2.1]oct-2-en-2-yl]ethenyl]-3,4,5,6-tetrahydro-4-hydroxy-2H-pyran-2-one.

17. Trans-(E)-6-[2-[3-(4-fluoro-3-chlorophenyl)-1,5-di(1-methylethyl) bicyclo[3.2.1]oct-2-en-2-yl]ethenyl]-3,4,5,6-tetrahydro-4-hydroxy-2H-pyran-2-one.

18. Trans-6-[2-[cis-endo-3-(4-methylphenyl)bicyclo[3.2.1]-pctan2-yl]ethyl]-3,4,5,6-tetrahydro-4-hydroxy-2H-pyran-2-one.

19. Trans-(E)-6-[2-[3-(4-fluoro-3-methylphenyl)-1,5-dimethylbicyclo[3.2.1]octa-2,6-dien-2-yl]ethenyl]-3,4,5,6-tetrahydro-4-hydroxy-2H-pyran-2-one.

20. Trans-(E)-6-[2-[cis-exo-3-(4-fluoro-3-methylphenyl)bicyclo[2.2.2]oct-5-en-2-yl]ethenyl]-3,4,5,6-tetrahydro-4-hydroxy-2H-pyran-2-one.

21. Trans-(E)-6-[2-[3-(4-fluoro-3-methylphenyl)-1,4-dimethylbicyclo[2.2.2]octa-2,5-dien-2-yl]ethenyl]-3,4,5,6-tetrahydro-4-hydroxy-2H-pyran-2-one.

22. Trans-(E)-6-[2-[trans-3-(3,4-ditrifluorophenyl)-1,4-di(2-methylethyl) bicyclo-[2.2.2]octan-2-yl]ethyl]-3,4,5,6-tetrahydro-4-hydroxy-2H-pyran-2-one.

23. Trans-(E)-6-[3-(3-methylphenylmethyl)-1-methylbicyclo[2.2.2]oct-2-en-2-yl]ethenyl]-3,4,5,6-tetrahydro-4-hydroxy-2H-pyran-2-one.

24. A hypocholesterolemic, hypolipidemic pharmaceutical composition comprising a therapeutically effective amount of a compound of claim 1 and a pharmaceutically acceptable carrier.

25. A method of inhibiting cholesterol biosynthesis in a patient in need of such treatment comprising administering a pharmaceutical composition defined in claim 24.

* * * * *